US00PP27356P3

(12) United States Plant Patent
Van Dijk

(10) Patent No.: US PP27,356 P3
(45) Date of Patent: Nov. 8, 2016

(54) ***ANTHURIUM* PLANT NAMED 'ANTHISXI'**

(50) Latin Name: ***Anthurium andreanum* L.**
Varietal Denomination: ANTHISXI

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 101 days.

(21) Appl. No.: 14/544,118

(22) Filed: Nov. 25, 2014

(65) Prior Publication Data

US 2016/0150711 P1 May 26, 2016

(51) Int. Cl.
*A01H 5/02* (2006.01)

(52) U.S. Cl.
USPC ..... Plt./369

(58) Field of Classification Search
USPC ..... Plt./369
See application file for complete search history.

(56) References Cited

PUBLICATIONS

Anthura Unlimited in Varieties, Anthurium Cut Flower & Pot Plant Culture, retrieved on Apr. 25, 2016, retrieved from the Internet at <http://www.grenethplants.nl/images/brochures/ANTHURIUM.pdf> pp. 1, 24 and 45.*

New Plants and Flowers, Two new and two improved cut anthuriums May 30, 2014, retrieved on Apr. 25, 2016, retrieved from the Internet at <http://www.newplantsandflowers.com/two-new-and-two-improved-cut-anthuriums/> 2 pp.*

New plants and Flowers, Two new and two improved cut anthuriums, May 30, 2014, retrieved on Apr. 25, 2016, retrieved from the internet at <http://www.newplantsandflowers.com/two-new-and-two-improved-cut-anthuriums/> 2pp.

EU Community Plant Variety Rights application No. 20141584, filed Jun. 10, 2014. (Document No. A201404005) 12 pp.

EU Community Plant Variety Rights, Official Gazette, Apr. 2014, Aug. 15, 2014, pp. 28 and 47. and p. 1.

Anthura Anthurium: Cut flower and pot plant culture, published Nov. 2014, pp. 1, 24 and 45.

* cited by examiner

*Primary Examiner* — June Hwu

(74) *Attorney, Agent, or Firm* — Jondle & Associates, P.C.

(57) ABSTRACT

A new and distinct variety of *Anthurium* plant named 'ANTHISXI' particularly characterized by having red spathes, a white spadix with a green tip, a long straight peduncle, little shoot formation, a tall plant habit and green foliage, is disclosed.

5 Drawing Sheets

Genus and species: *Anthurium andreanum* L.
Variety denomination: 'ANTHISXI'.

BACKGROUND OF THE NEW PLANT

The present invention comprises a new and distinct variety of *Anthurium*, botanically known as *Anthurium andreanum* L., and hereinafter referred to by the variety name 'ANTHISXI'. The new variety originated from a hybridization made in July 2004 in Bleiswijk, The Netherlands. The female parent is a red *Anthurium* cutflower plant designated '5139-08' (unpatented), and the male parent was a red *Anthurium* cutflower plant designated '3282-06' (unpatented).

A single plant was selected in July 2007 and has been asexually reproduced repeatedly by meristem tissue culture in Bleiswijk, The Netherlands over a seven-year period. The present invention has been found to retain its distinctive characteristics through successive asexual propagations.

Plant Breeder's Rights for this variety have been applied for in Europe on Jun. 10, 2014. 'ANTHISXI' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands.

1) Red spathe;
2) White spadix with green tip;
3) Long straight peduncle;
4) Little shoot formation;
5) Tall plant habit; and
6) Green foliage.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 300-week old plant grown in a greenhouse in Bleiswijk, The Netherlands in 2014.

DESCRIPTION OF THE NEW VARIETY

Figure 1:
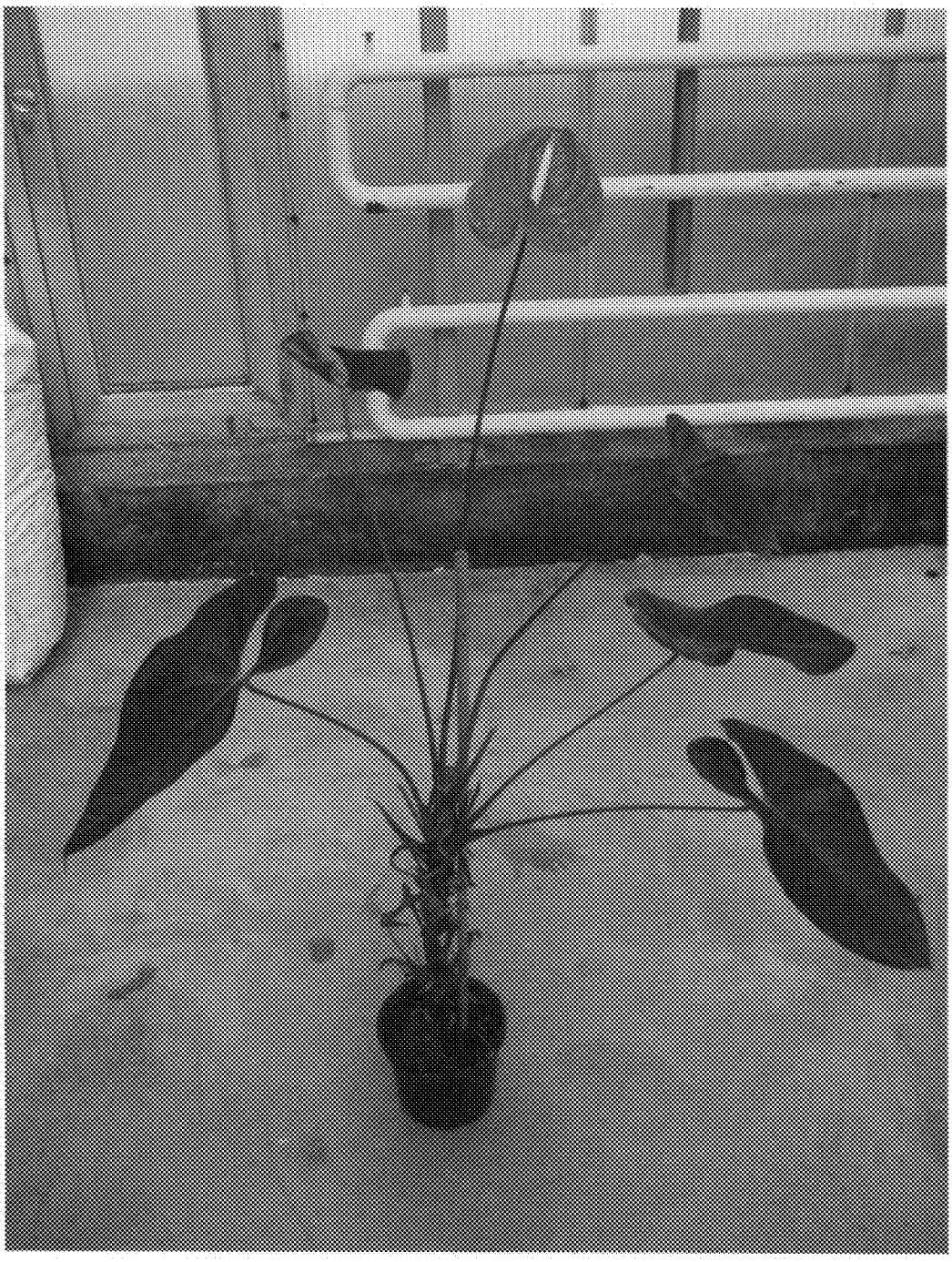
FIG. 1 shows the overall plant habit, including blooms and foliage.
Figure 2:
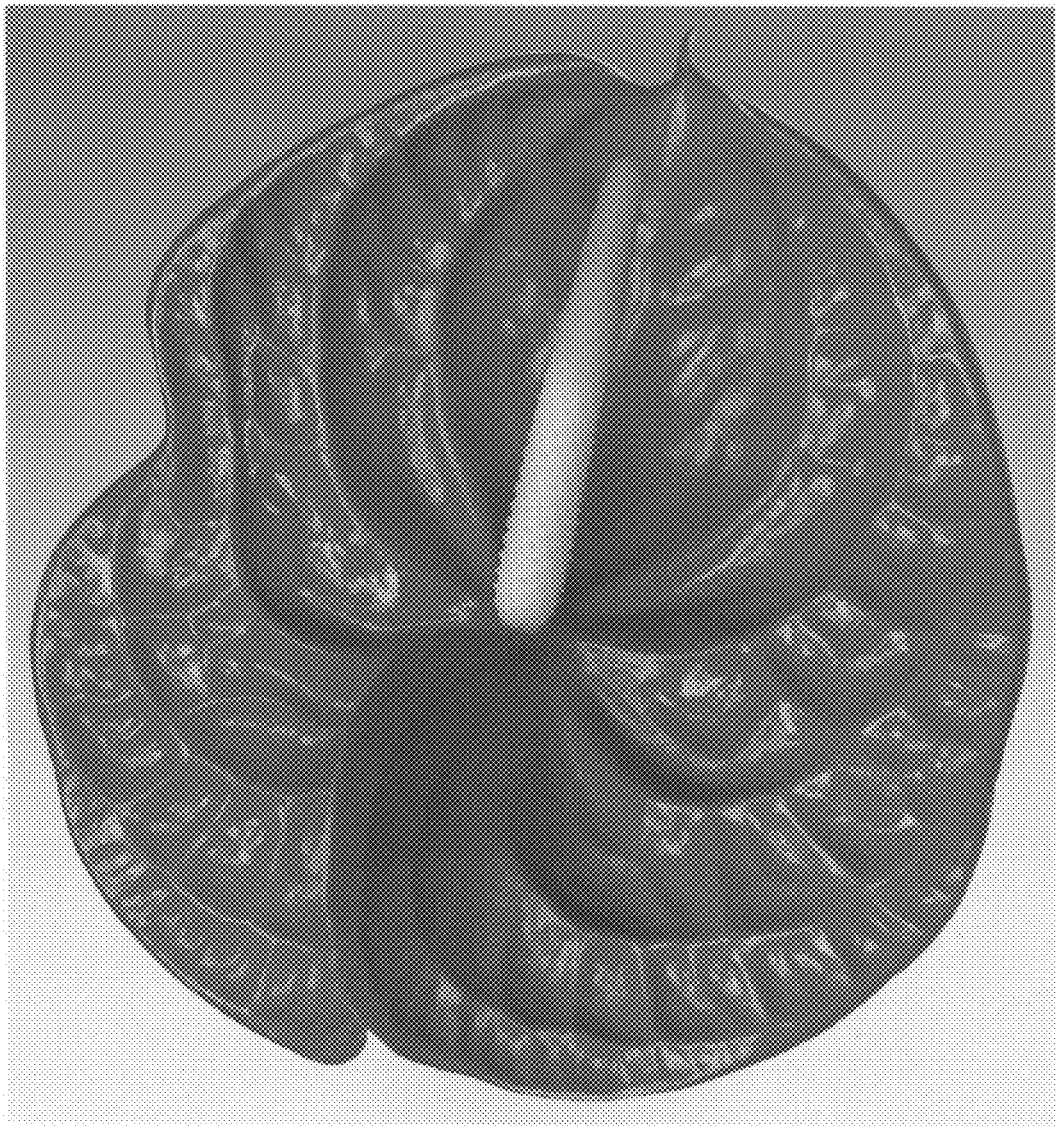
FIG. 2 shows a close-up of the mature spathe.
Figure 3:
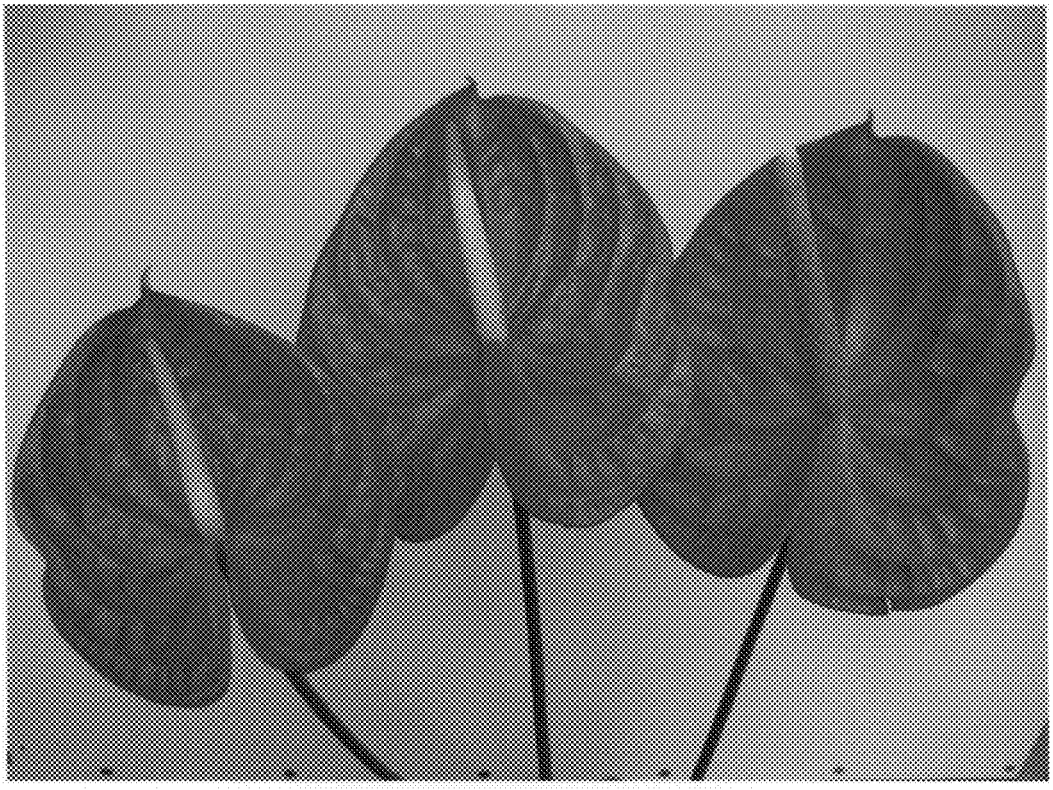
FIG. 3 shows three spathes at different stages of development.
Figure 4:
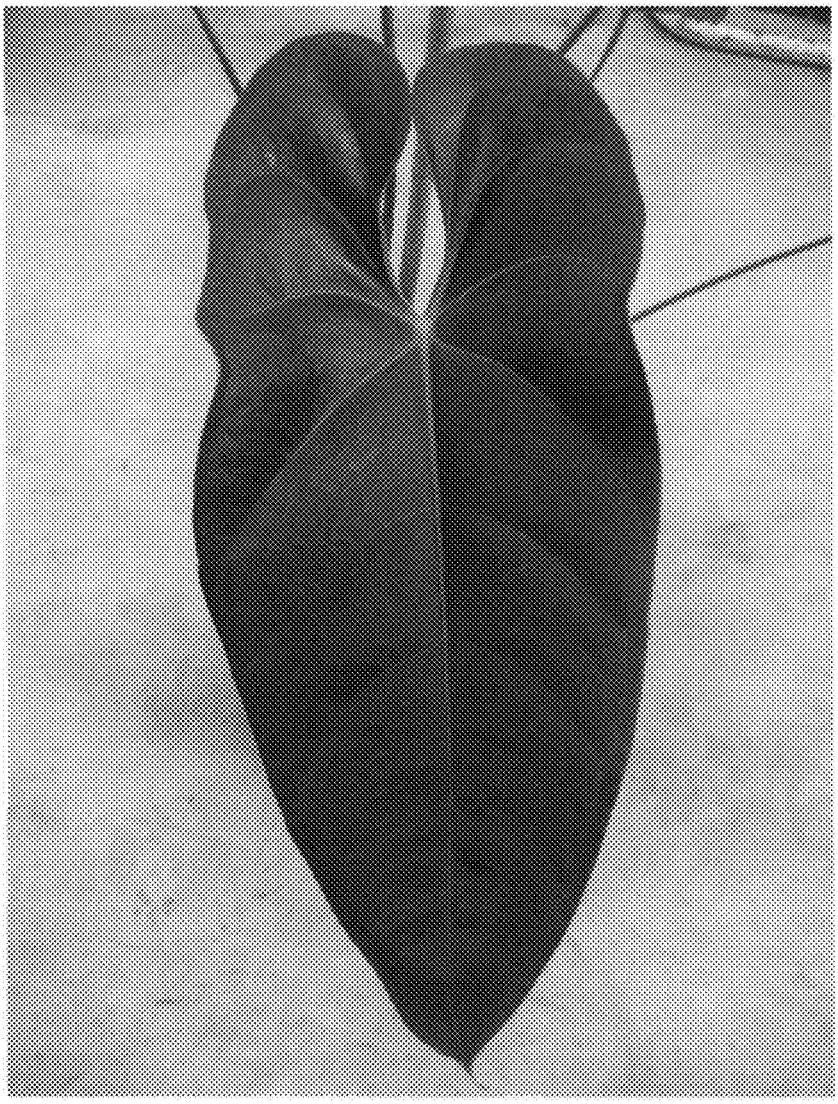
FIG. 4 shows the upper leaf surface.
Figure 5:
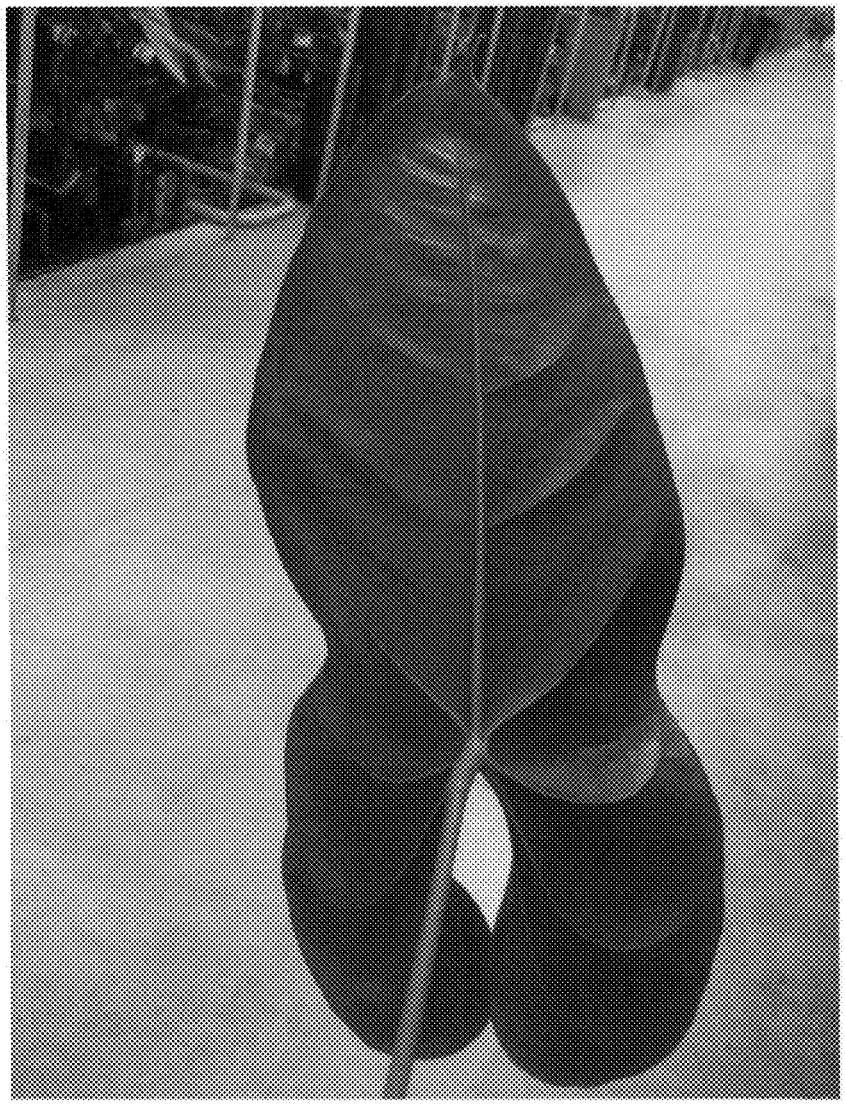
FIG. 5 shows the lower leaf surface.

The following detailed description sets forth the distinctive characteristics of 'ANTHISXI'. The data which define these characteristics were collected from asexual reproductions carried out in Bleiswijk, The Netherlands. The plant history was taken on 300-week old plants which were planted from tissue culture in 7-centimeter pots and grown in a glass greenhouse between 19° C. and 24° C. Observations were made in September 2014. Color readings were taken under 5000 lux natural light in the greenhouse. Color references are primarily to The R.H.S. Colour Chart of The Royal Horticultural Society of London (R.H.S.) (2001)

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHISXI'.

Parentage:

*Female parent*.—*Anthurium* plant '5139-08' (unpatented).

*Male parent*.—*Anthurium* plant '3282-06' (unpatented).

Plant:

*Propagation*.—Meristem tissue culture.

*Root description*.—Creamy white-colored roots with hairy lateral roots having yellow-colored root tips.

*Time to produce a finished flowering plant*.—50 to 70 weeks for a full grown, cutflower plant.

*Growth habit*.—Herbaceous perennial.

*Height* (*measured from soil, including inflorescence*).—100.0 cm to 120.0 cm.

*Width* (*measured from leaf tips*).—80.0 cm to 120.0 cm.

Leaves:

*Immature leaves*.—Length: 5.0 cm to 20.0 cm. Width: 3.0 cm to 12.0 cm. Color: Upper surface: RHS 146A. Lower surface: RHS 148A. Texture (both upper and lower surfaces): Shiny flat/no texture.

*Mature leaves*.—Length (fully expanded): 30.0 cm to 40.0 cm. Width: 15.0 cm to 20.0 cm. Shape: Ovate. Apex: Acuminate. Base: Cordate. Leaf blade angle with the petiole: Between 90 degrees and 120 degrees. Leaf margin: Entire. Color: Upper surface: RHS 139A. Lower surface: RHS 146A. Texture: Dull, flat to slightly blistered. Venation: The veins protrude at the underside of the leaves. Venation color: Upper surface: RHS 144B. Lower surface: RHS 145A.

*Lobes*.—Arrangement: Slightly overlapping. Length of lobes of mature leaf blades: 9.0 cm to 11.0 cm. Width of lobes of mature leaf blades: 7.0 cm to 8.0 cm. Distance from petiole/leaf junction to highest point on lobes of mature leaf blades: 3.0 cm to 4.0 cm.

*Petiole*.—Cross-section: Round. Diameter: 0.5 cm to 0.8 cm. Length: 32.0 cm to 38.0 cm for a mature leaf size. Color: Mature leaf: RHS 144A. Immature leaf: RHS 152A. Cataphyl color surrounding the petiole: Outside: RHS 144A. Inside: RHS 146C.

*Geniculum*.—Length: 2.0 cm to 3.0 cm. Width: 0.6 cm to 0.7 cm. Color: RHS 145A.

Inflorescence:

*Arrangement*.—Well above the leaf canopy.

*Flowering habit* (*length of flowering season*).—Continuous.

*Number of inflorescences per plant*.—5 to 7 per plant per year.

*Fragrance*.—Absent.

*Longevity of inflorescence on plant*.—Over 15 weeks.

*Longevity of the flower as a cut flower*.—23 days to 26 days.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 100 degrees and 120 degrees; the spathe stands on a wiry peduncle about 20.0 cm to 30.0 cm above the foliage.

*Shape*.—Cordate.

*Apex*.—Broad acute.

*Base*.—Touching.

*Base shape*.—Cordate.

*Texture*.—Shiny and blistered.

*Margin*.—Entire.

*Size*.—Height: 60.0 cm to 80.0 cm (peduncle length at maturity). Length: 14.0 cm to 17.0 cm. Width: 12.0 cm to 15.0 cm.

*Color*.—Just fully open: Upper surface: RHS 45A. Lower surface: RHS 46C. 5 to 8 weeks after opening: Upper surface: RHS 45B. Lower surface: RHS 50A.

Peduncle:

*Shape*.—Wiry.

*Cross-section*.—Round.

*Length*.—60.0 cm to 80.0 cm.

*Diameter*.—0.5 cm to 0.8 cm.

*Color*.—RHS 173B with RHS 144A towards the base of the peduncle.

Flowering time:

*General*.—One small rooted untreated tissue culture plant of 4.0 cm tall will flower after 6 to 8 months, depending on the season, and 1 blossom will appear at a time. More blossoms appear successively after every 6 to 10 weeks so that there is a continuous production of cutflowers. Smaller blossoms may occur on less mature plants.

Spadix:

*Size*.—Length: 7.0 cm to 8.0 cm (depending on flower size). Width (at apex): 0.5 cm to 0.6 cm. Width (at base): 0.9 cm to 1.1 cm.

*Shape*.—Columnar.

*Angle from spadix tip to peduncle*.—125 degrees to 140 degrees.

*Texture*.—When the spathe is unfurling the spadix is smooth. When the spadix matures, very small stigmata protrude. The stigmata are evenly distributed round the spadix. The spadix matures from base to top, slowly giving the spadix a somewhat coarse appearance.

*Color*.—Immature: RHS 153A. Mature: RHS 158C. Ages to: RHS 153B.

Flowers:

*Quantity per spadix*.—600 to 800.

*Spadix flower arrangement*.—Bisexual, rounded in cross-section.

*Shape*.—Very small.

*Size*.—Length: 0.1 cm to 0.2 cm. Diameter (maximum): 0.1 cm.

*Color*.—RHS 158C.

Reproductive organs:

*Stamens*.—Anthers and filaments are not clearly visible on the spadix.

*Pollen amount*.—Abundant pollen production.

*Pollen color*.—RHS 155A.

*Pistil*.—Quantity: 600 to 800 on mature spadix. Length: Less than 0.1 cm. Color: RHS 158B.

*Style*.—Very small.

*Stigma*.—Shape: Round. Diameter: Less than 0.1 cm. Color: RHS 158B.

*Ovary*.—Produced, but too small to observe.

*Ovary color*.—Not measured, too small.

Disease and Pest Resistance: Not observed to date.

Fruit and Seed Set: None observed.

COMPARISON WITH PARENTAL AND COMMERCIAL VARIETIES

'ANTHISXI' differs from the female parent plant '5139-08' (unpatented) in that 'ANTHISXI' has a firm, sturdy stem and a white spadix with a green tip, whereas '5139-08' has a shaky and curved stem and a white spadix with a yellow tip.

'ANTHISXI' differs from male parent plant '3282-06' (unpatented) in that 'ANTHISXI' has a firm, sturdy stem and a round spathe, whereas '3282-06' has a firm but curved stem and an oval spathe.

'ANTHISXI' differs from commercial variety 'Tropical' (unpatented) in that 'ANTHISXI' has a firm, sturdy stem, small leaf size and a relatively thin and short spadix, whereas 'Tropical' has a stem that is often curved, large leaf size and a thick and long spadix.

'ANTHISXI' differs from commercial variety 'ANTHAQAL' (unpatented) in that 'ANTHISXI' has a thin and short spadix, small leaf size and light green spadix tip, whereas 'ANTHAQAL' has a thick and long spadix, intermediate leaf size and yellow spadix tip.

I claim:

1. A new and distinct variety of *Anthurium* plant named 'ANTHISXI', substantially as illustrated and described herein.

* * * * *